United States Patent [19]

Brown et al.

[11] 3,953,536

[45] Apr. 27, 1976

[54] CATALYST TREATMENT

[75] Inventors: Alistair Chalmers Ramsay Brown; Norman Andrew Dykes; John Kenneth January; Ivan James Samuel Lake, all of Stockton-on-Tees, England

[73] Assignee: Imperial Chemical Industries Limited, London, England

[22] Filed: May 19, 1975

[21] Appl. No.: 578,812

Related U.S. Application Data

[62] Division of Ser. No. 346,859, April 2, 1973, Pat. No. 3,898,182.

[30] Foreign Application Priority Data

Apr. 24, 1972 United Kingdom............... 18824/72

[52] U.S. Cl............................................. 260/668 A
[51] Int. Cl.$^2$..................... C07C 5/24; C07C 15/08
[58] Field of Search................................. 260/668 A

[56] References Cited
UNITED STATES PATENTS

| | | | |
|---|---|---|---|
| 3,836,594 | 9/1974 | Sampson et al................. | 260/668 A |
| 3,898,297 | 8/1975 | Sampson et al................. | 260/668 A |

*Primary Examiner*—C. Davis
*Attorney, Agent, or Firm*—Cushman, Darby & Cushman

[57] ABSTRACT

Catalysts which comprise silica are rendered less susceptible to physical damage during processing with aqueous liquids by pre-steaming them.

9 Claims, No Drawings

CATALYST TREATMENT

This is a division of application Ser. No. 346,859, filed Apr. 2, 1973, now U.S. Pat. No. 3,898,182.

This invention relates to catalyst treatment.

In certain processes for the treatment of catalysts comprising silica they are contacted with aqueous liquids, for example water or aqueous solutions or slurries. They may be contacted with aqueous solutions in order that on evaporation of the water the catalyst may be impregnated with a solute; this may, for example, after calcination, produce a supported catalyst, for example, a supported metal catalyst when the solute is a metal compound. Silica or silica/alumina catalysts may also be improved by exposure to liquid water at a temperature in excess of 100°C or to super-critical water at elevated pressure. Certain catalysts comprising silica, especially silica/alumina catalysts are, however, susceptible to physical damage during contact with the aqueous liquid, especially if they are dry (for example, containing less than 25 percent and particularly less than 10 percent of water before such exposure). Such catalysts have in general been dried in an inert gas, for example air, at a temperature of 150° to 750°C.

It is an object of this invention to reduce the damage caused to such catalysts on contact with aqueous liquids.

According to this invention, in a process of treatment of a catalyst, which comprises silica and which is susceptible to physical damage during exposure to aqueous liquids, by contact with an aqueous liquid, the catalyst is conditioned to make it less susceptible to such damage by exposing it to steam at less than its saturated vapour pressure before such treatment.

The catalyst may be a silica/alumina cracking catalyst, especially one of the bead type.

It is prefered that the steam should be at a temperature above its condensation temperature by 10° to 300°C, and more preferably by 100° to 250°C at the pressures applied.

The process is suitably carried out by passing superheated steam through the catalyst. This may be carried out at a weight hourly space velocity of 0.05 to 5, and preferably 0.1 to 0.5.

The catalyst is preferably held at a temperature in the range 150° to 600°C, and preferably 300° to 400°C during the exposure to steam.

The treatment with steam is preferably carried out at a pressure of steam of 0.5 to 30, and more preferably 2 to 8 bars absolute.

The catalyst is preferably exposed to steam for a period of 1 to 100 hours, and more preferably 15 to 40 hours. Thereafter the steam may be replaced, if desired, by an inert non-condensing gas, for example oxygen, nitrogen or air before cooling the catalyst and then exposing it to the aqueous liquid.

The aqueous liquid is suitably water. It may in some cases contain acid or alkali. The exposure preferably takes place at a temperature of 100° to 374°C (the critical point of water) and is at a sufficient pressure to maintain the water in the liquid phase (which is normally between 1 bar and 220 bars). More commonly, pressures in the range 2 to 100 bars and temperatures of 130° to 270°C are used.

The time of exposure to aqueous liquid is normally 5 minutes to 500 hours and is more commonly in the range 30 minutes to 100 hours.

Suitable silica/alumina catalysts for use in isomerising mixtures of alkyl benzenes having at most 4 carbon atoms in each alkyl group, especially those having two alkyl groups, for example the xylenes, include those having an analysis of 1 to 40 percent, and preferably from 6 to 30 percent by weight of alumina, the balance being substantially silica. Before exposure to liquid water they preferably have a surface area in the range 200 to 700 square meters/gram, and preferably 350 to 700 square meters/gram. Their mean pore diameter is preferably at least 10A, more preferably at least 20A, and yet more preferably at least 40A, and may be in the range 10 to 200A.

In general the mean pore size of these catalysts increases during the treatment by, for example, 20 to 300A. The severity and duration of the conditions under which the exposure of the catalyst to the water occurs may be adjusted in terms of the desired increase in pore size to be obtained. Desired pore sizes of the product may be, for example, 50 to 400A, and preferably 100 to 250A. It is believed that other changes also occur in the catalysts during exposure to water.

After exposure to the aqueous liquid the catalyst is usually dried before use. It is sometimes found that a catalyst suffers physical damage during drying. This may, however, be overcome by drying the catalyst, at least initially, in a steam atmosphere. This may be carried out at a temperature in the range 150° to 250°C, and preferably 160° to 200°C. Preferably no air is present. Suitable partial pressures of steam are 1 to 3 bars absolute, and preferably 1 to 2 bars absolute. Preferably the steam is at a temperature of 50° to 100°C above its condensation point at the partial pressure applying. It is convenient to pass superheated steam through a bed of the catalyst in order to dry it. This enables temperature losses in the bed due to the latent heat of evaporation of water in the catalyst and to thermal losses from the bed to be made good by passing the steam through the bed at a suitable rate, which may be in the range 0.05 to 50, and preferably 0.1 to 10, expressed as a weight hourly space velocity.

The catalyst, may if desired, be calcined to effect complete drying.

In the isomerisation of xylenes, for example the isomerisation of one or more xylenes containing less than an equilibrium concentration of paraxylene to produce a product having a higher concentration of paraxylene using a silica/alumina catalyst, the exposure of the catalyst to liquid water at a temperature in excess of 100°C to super-critical water generally reduces the tendency for disproportionation to occur. It may also reduce carbon lay-down on the catalyst and may also increase its activity.

Isomerisation of xylenes is preferably carried out at a temperature in the range 200° to 600°C, and preferably 300° to 500°C. It is preferably carried out at a pressure of 0.5 to 50 atmospheres, and more preferably at a pressure in the range 1 to 5 atmospheres. It may be carried out, if desired, in the presence of small amounts of, for example, steam or ammonia.

EXAMPLE

A batch of silica/alumina bead catalyst containing 10% alumina and having a surface area of 450 $m^2g^{-1}$ and a pore volume of 0.57 $cm^3g^{-1}$, and a mean pore diameter of 51A, was placed in a stainless steel tubular reactor and heated to 300°C. Superheated steam at this temperature and 5.1 atmospheres pressure was passed through the catalyst bed at a WHSV of 0.17, whereupon the temperature rose and was stabilised at 350°C. The treatment was continued for 40 hours; the steam replaced by air and the catalyst calcined at 550°C for 5 hours. At this stage the surface area was found to be 300 $m^2g^{-1}$ and pore volume 0.55 $cm^3g^{-1}$, and the mean pore diameter 73A. On immersion of a sample in cold water, 2 percent of the beads cracked. (On immersion of a sample of the starting material, about 38% of the beads either cracked or split into several fragments).

50 g. of this catalyst were placed in an autoclave with 150 ml. of water and hydrothermally treated at 204°C and 16.6 atmospheres for 4.5 hours.

25 g. of this material, still wet from the treatment, was placed in a lagged vertical glass tube. Steam at 165°C and atmospheric pressure was then passed over it at a rate of 600 g.hr.$^{-1}$. After 70 minutes, when all of the catalyst bed had reached to within 10°C of the inlet temperature, the steam was replaced by air flowing at 200 l/hr$^{-1}$. The air temperature was gradually increased to 430°C over 5.5 hours and then the catalyst was cooled and examined.

The sample was found to contain 2.5 percent damaged beads. The surface area and pore volume were 189 $m^2g^{-1}$ and 0.52 $cm^3g^{-1}$ and the mean pore diameter was 110A.

We claim:

1. A process which comprises isomerising a mixture of xylenes containing less than an equilibrium concentration of paraxylene at a temperature in the range 200° to 600°C, at a pressure in the range 0.5 to 50 atmospheres by contacting the mixture with a silica catalyst prepared by a process which comprises exposing a silicia catalyst, which is normally susceptible to damage during exposure to an aqueous liquid, to steam at less than its saturated vapour pressure and then contacting the catalyst with the aqueous liquid and drying the catalyst after exposure to the aqueous liquid.

2. A process as claimed in claim 1 in which the steam is at a temperature which is above its condensation temperature by 10° to 300°C at the pressures applied.

3. A process as claimed in claim 1 in which the steam used is superheated steam.

4. A process as claimed in claim 1 in which after exposure to steam but prior to treatment with the aqueous liquid, the steam is replaced by an inert noncondensing gas.

5. A process as claimed in claim 1 in which exposure to the aqueous liquid takes place at a temperature in the range of 100° to 374°C and at a pressure sufficient to maintain the water in the liquid phase.

6. A process as claimed in claim 1 in which the catalyst, after exposure to the aqueous liquid, is dried, at least initially, in a steam atmosphere.

7. A process as claimed in claim 1 in which superheated steam is used for drying.

8. A process as claimed in claim 7 in which the catalyst is calcined after being dried with steam.

9. A process as claimed in claim 1 in which the catalyst is a silica/alumina catalyst.

* * * * *